United States Patent
Freudenthal

(10) Patent No.: US 10,182,822 B2
(45) Date of Patent: Jan. 22, 2019

(54) EMBOLIZATION DEVICE

(75) Inventor: Franz Freudenthal, La Paz (BO)

(73) Assignee: PFM MEDICAL AG, Cologne (DE)

( * ) Notice: Subject to any disclaimer, the term of this patent is extended or adjusted under 35 U.S.C. 154(b) by 485 days.

(21) Appl. No.: 12/673,770

(22) PCT Filed: Jun. 25, 2008

(86) PCT No.: PCT/EP2008/005119
§ 371 (c)(1),
(2), (4) Date: Feb. 16, 2010

(87) PCT Pub. No.: WO2009/021577
PCT Pub. Date: Feb. 19, 2009

(65) Prior Publication Data
US 2011/0295303 A1    Dec. 1, 2011

(30) Foreign Application Priority Data
Aug. 14, 2007   (DE) .................. 10 2007 038 446

(51) Int. Cl.
*A61B 17/12* (2006.01)
*A61B 17/00* (2006.01)

(52) U.S. Cl.
CPC .... *A61B 17/12022* (2013.01); *A61B 17/1215* (2013.01); *A61B 17/12145* (2013.01); *A61B 17/12154* (2013.01); *A61B 17/1214* (2013.01); *A61B 2017/00477* (2013.01); *A61B 2017/00867* (2013.01); *A61B 2017/12054* (2013.01)

(58) Field of Classification Search
CPC .................. A61B 17/12022; A61B 2017/1205–2017/12095

USPC ....... 606/108, 200; 623/1.11, 1.12; 128/831, 128/843
See application file for complete search history.

(56) References Cited

U.S. PATENT DOCUMENTS

| | | | | |
|---|---|---|---|---|
| 5,250,071 A * | 10/1993 | Palermo | .................. | 606/198 |
| 5,382,259 A * | 1/1995 | Phelps et al. | .................. | 606/151 |
| 5,421,348 A * | 6/1995 | Larnard | .................. | 600/585 |
| 5,639,277 A * | 6/1997 | Mariant et al. | .................. | 606/191 |
| 5,749,891 A * | 5/1998 | Ken et al. | .................. | 606/200 |

(Continued)

FOREIGN PATENT DOCUMENTS

| | | |
|---|---|---|
| DE | 698 31 889 | 4/2006 |
| DE | 698 33 699 | 8/2006 |

(Continued)

OTHER PUBLICATIONS

International Search Report and Written Opinion from PCT Appln. No. PCT/EP2008/005119 dated Apr. 6, 2009.

*Primary Examiner* — Darwin Erezo
*Assistant Examiner* — Jonathan Hollm
(74) *Attorney, Agent, or Firm* — Grossman, Tucker, Perreault & Pfleger, PLLC

(57) ABSTRACT

In an embolization device (1) with a main body (3) and with at least one thrombogenic fiber (2), which main body can be converted from an elongate primary shape to a secondary shape, the at least one thrombogenic fiber (2) is arranged in a configuration wound around the main body. In a method for producing an embolization coil of this kind, a primary coil (30) forming a main body (3) of the embolization coil (1) has at least one thrombogenic fiber (2) wound around it, and the primary coil (30) is converted in shape to a secondary coil.

23 Claims, 8 Drawing Sheets

(56) References Cited

U.S. PATENT DOCUMENTS

Figure 1:
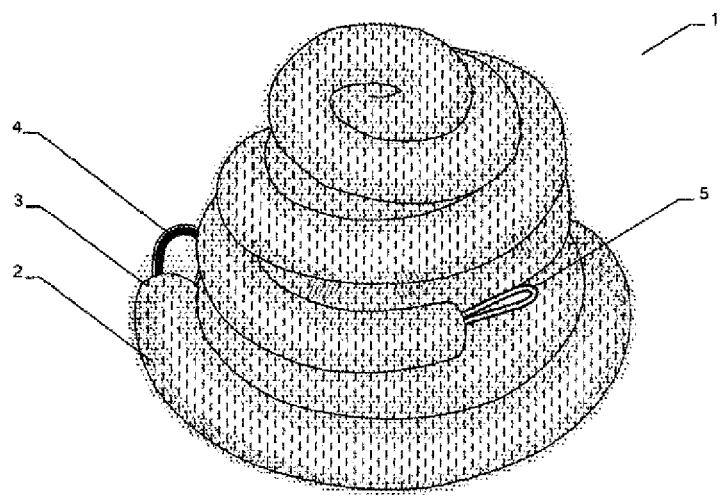

| | | | |
|---|---|---|---|
| 5,766,160 A * | 6/1998 | Samson | A61B 17/12022 606/1 |
| 5,895,391 A * | 4/1999 | Farnholtz | 606/108 |
| 5,911,717 A | 6/1999 | Jacobsen et al. | |
| 6,013,084 A * | 1/2000 | Ken et al. | 606/108 |
| 6,187,027 B1 | 2/2001 | Mariant et al. | |
| 6,280,457 B1 * | 8/2001 | Wallace et al. | 606/200 |
| 6,338,736 B1 * | 1/2002 | Boosfeld et al. | 606/191 |
| 6,458,137 B1 * | 10/2002 | Klint | 606/108 |
| 6,790,218 B2 * | 9/2004 | Jayaraman | 606/191 |
| 6,793,673 B2 * | 9/2004 | Kowalsky et al. | 623/2.36 |
| 7,326,225 B2 | 2/2008 | Ferrera et al. | |
| 8,845,676 B2 | 9/2014 | Monstadt et al. | |
| 2002/0151926 A1 * | 10/2002 | Wallace et al. | 606/200 |
| 2004/0002731 A1 * | 1/2004 | Aganon et al. | 606/200 |
| 2005/0021074 A1 * | 1/2005 | Elliott | 606/200 |
| 2005/0101968 A1 | 5/2005 | Dadourian | |
| 2005/0192619 A1 * | 9/2005 | Teoh et al. | 606/200 |
| 2006/0036281 A1 * | 2/2006 | Patterson et al. | 606/200 |
| 2006/0116714 A1 * | 6/2006 | Sepetka et al. | 606/200 |
| 2006/0135986 A1 * | 6/2006 | Wallace et al. | 606/200 |
| 2006/0271097 A1 * | 11/2006 | Ramzipoor et al. | 606/200 |
| 2006/0276827 A1 * | 12/2006 | Mitelberg et al. | 606/200 |
| 2007/0123928 A1 * | 5/2007 | Farnan | 606/200 |
| 2008/0097462 A1 * | 4/2008 | Mitelberg et al. | 606/108 |

FOREIGN PATENT DOCUMENTS

| | | |
|---|---|---|
| EP | 0 778 005 | 6/1997 |
| EP | 1 584 298 | 10/2005 |
| EP | 1 738 697 | 1/2007 |
| JP | 8-131553 | 5/1996 |
| JP | 2001-079011 | 3/2001 |
| JP | 2005-237952 | 9/2005 |
| WO | 95/25480 | 9/1995 |
| WO | 96/40024 | 12/1996 |
| WO | 2006/032291 | 3/2006 |
| WO | 2007/070792 | 6/2007 |

* cited by examiner

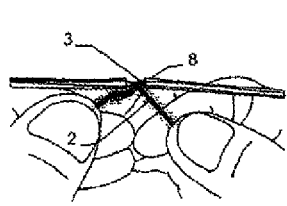
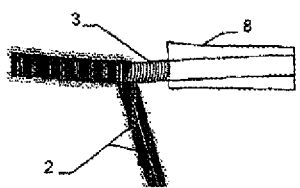
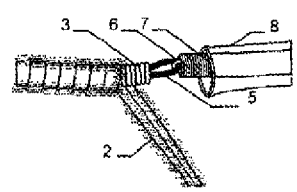
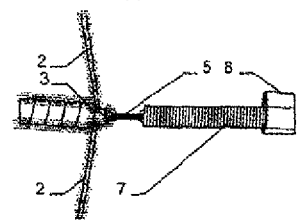
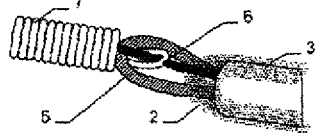
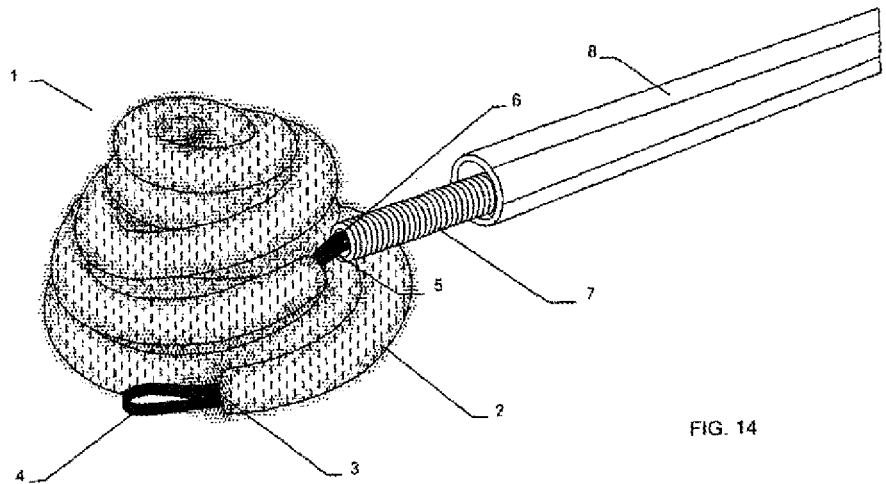

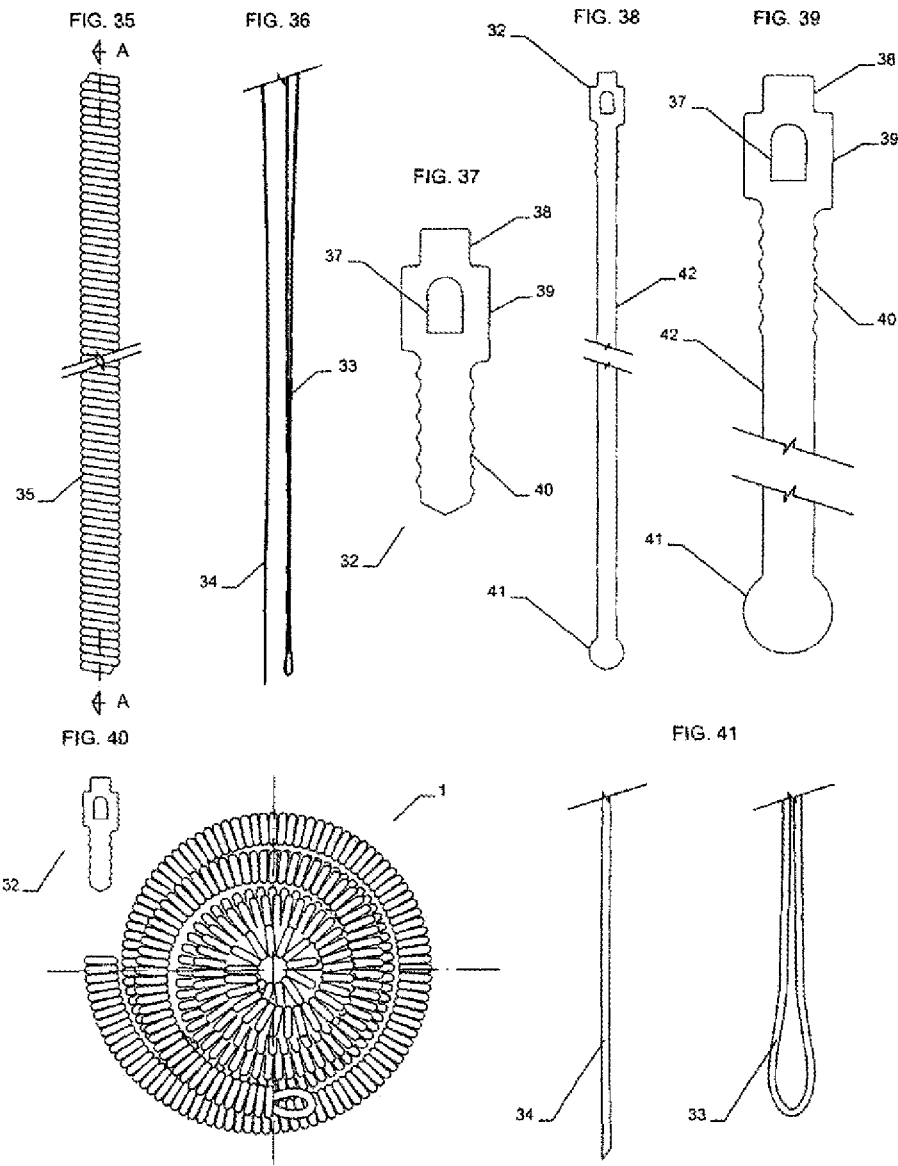

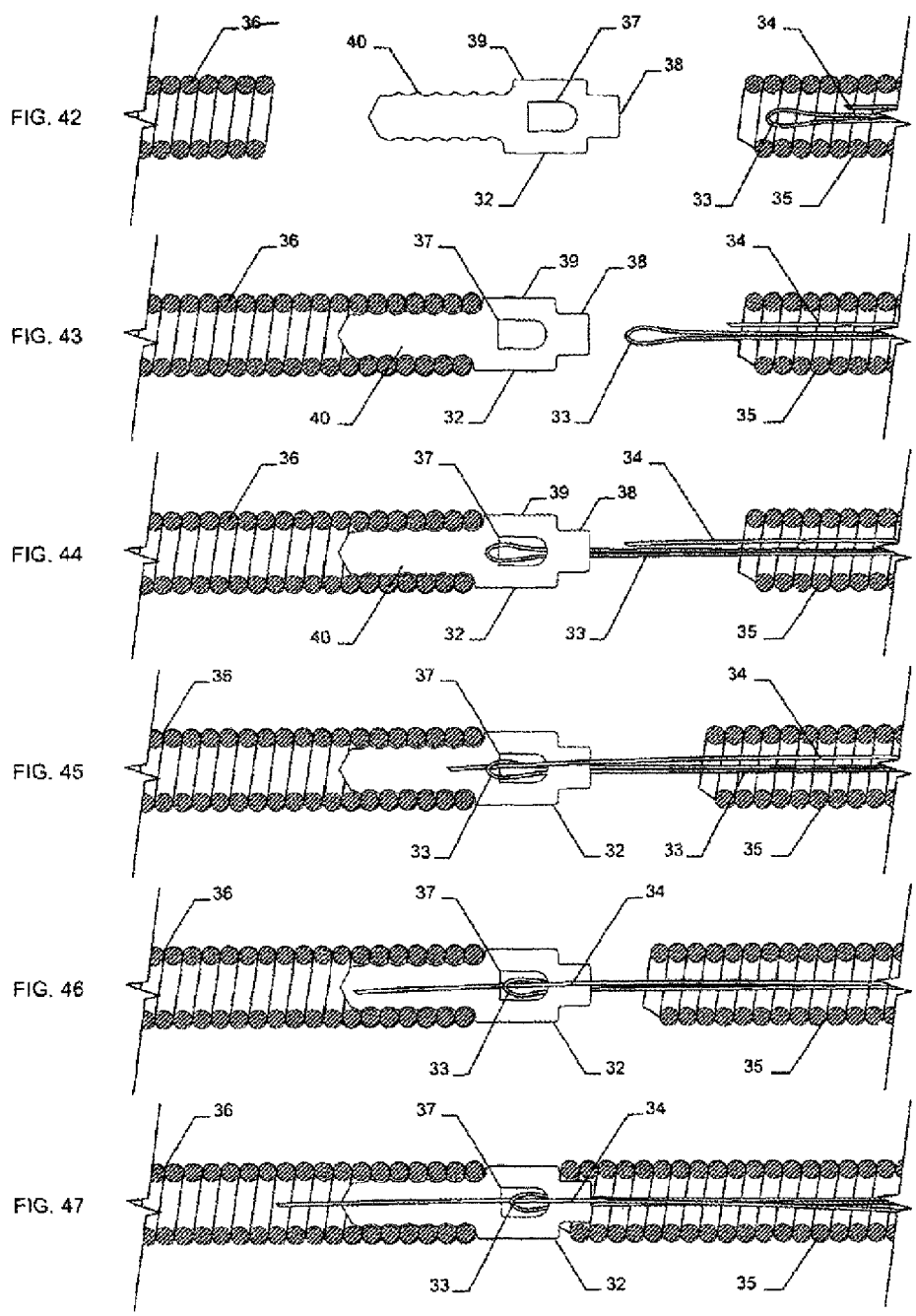

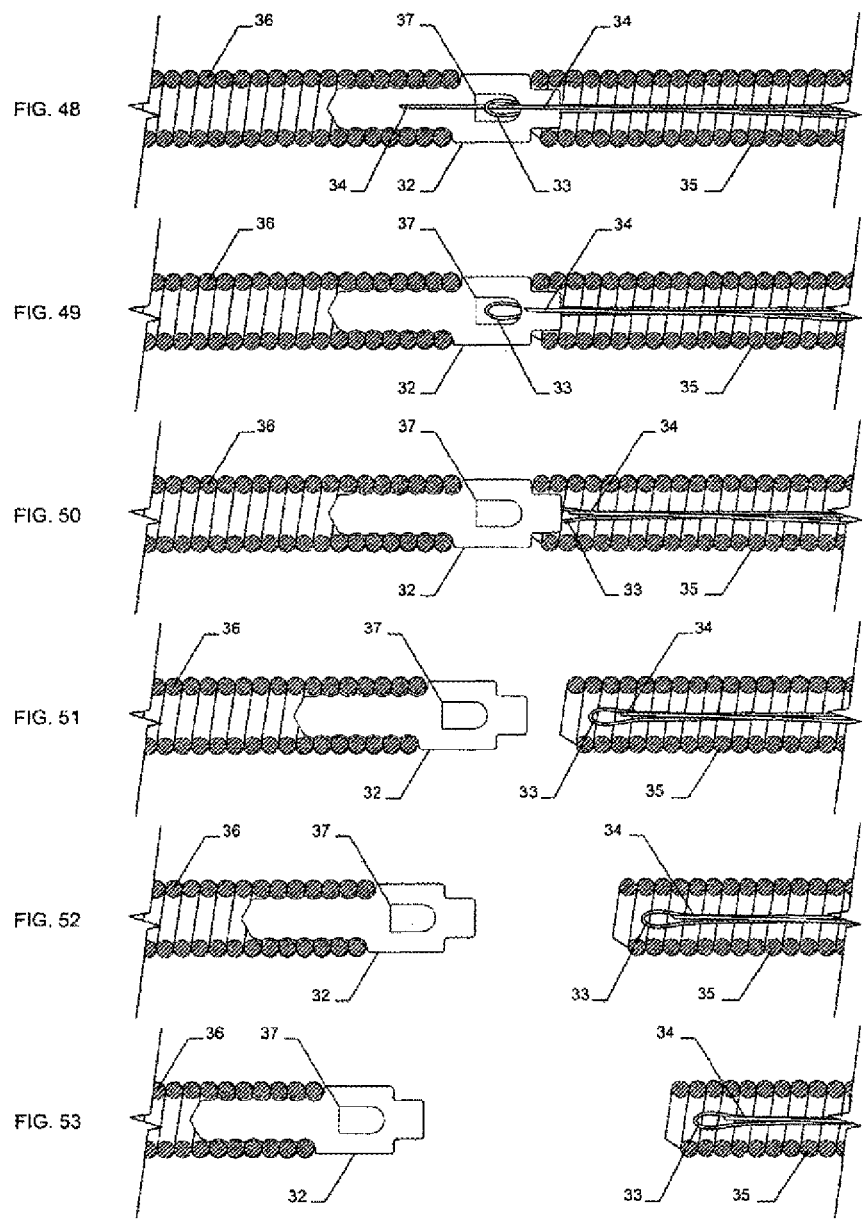

EMBOLIZATION DEVICE

This United States National Stage Application claims the benefit of International Application No. PCT/EP2008/005119 filed on 25 Jun. 2008, which claims priority to German Application No. 10 2007 038 446.9 filed on 14 Aug. 2007, both of which are respectively incorporated herein in their entirety by reference.

The invention relates to an embolization device with a main body and with at least one thrombogenic fiber, which main body can be converted from an elongate primary form to a secondary form, and a method for producing such an embolization device.

Embolization devices are known in many different forms. They are used for the occlusion or partial occlusion of a vessel, organ channel or other opening in the body. Such an occlusion or partial occlusion can be used to create an artificial embolism, e.g. in order to bring internal bleeding under control or for another purpose. In this connection, it is known for an embolization device of this kind to be expanded by a balloon catheter at the desired location or, alternatively, for the embolization device to be made of a self-expanding material, for example a shape-memory material. The embolization device in this case can be conveyed minimally invasively through a catheter to the desired site in the body of a human or animal and, in the elongate primary form, can be pushed out of the catheter at said site, as a result of which the embolization device adopts its predefined secondary form. This can include a wide variety of forms, for example that of a coil or an irregularly rolled-up three-dimensional figure. In each case, it is also known in principle to apply thrombogenic fibers to the embolization device in order to additionally strengthen the embolization effect.

In this connection, EP 0 750 480 B1, for example, discloses that thrombogenic fibers made of commercially available Z-twist Dacron fiber material are arranged, at regular intervals along the length of a coil, between closely adjacent windings of said coil. These thrombogenic fibers then protrude radially out between the windings of the primary coil. A similar structure is also known from JP-8131553. Likewise, JP-2001079011 proposes a similar structure.

According to DE 698 31 889 T2, an embolization device is disclosed in which a resilient wire wound up in a coil shape is provided on its outer surface with cuts, which on the one hand serve to improve the flexibility of the coiled wire and on the other hand serve for the application of thrombogenic fibers. The fibers can be knotted into the wire, secured thereon by means of an adhesive, melted on, or applied by another connecting method.

According to DE 698 26 275 T2, an embolization device is proposed comprising a primary coil that can be converted to various secondary forms. Thrombogenic fibers are braided in along this primary coil. These fibers are secured at one end on respective windings and are threaded through some of the windings lying between these, such that loops of the thrombogenic fibers protrude from the outside of the primary coil. Alternatively, it discloses a braided sheath made of a fibrous material that surrounds the primary walls. A similar structure is also disclosed in DE 698 33 699 T2, in which thrombogenic fibers are likewise threaded through the turns of a primary coil and of a secondary coil. In this case too, loops of thrombogenic fibers protrude from the coil. The vaso-occlusive coil according to DE 698 26 275 T2 also has a corresponding structure.

Fibers protruding from the circumference of the helix or coil are disclosed not only in U.S. Pat. No. 6,187,027 B1 and EP 1 584 298 A1, but also in JP-2005237952. A corresponding structure is also known from JP-8131553 and JP-2001079011.

According to DE 698 31 889 T2, slits are provided along the coil, or the primary material thereof, and suitable fibers protrude from these slits.

Another alternative solution for applying thrombogenic fibers to an occlusion coil is disclosed in EP 0 778 005 A1 and JP-9276280. Here, a large number of strands of thrombogenic fibers are routed internally through the turns of the occlusion coil. The ends of the thrombogenic fiber strands are connected to one another.

For the occlusion of an opening located in the body of a human or animal, the above-described embolization devices are already better suited than embolization devices that have no thrombogenic fibers. Nevertheless, there is a risk of the protruding thrombogenic fibers coming loose from the embolization device and leading to blood clots at an undesired location.

The object of the present invention is therefore to develop an embolization device according to the preamble of claim 1, and a method for producing such an embolization device, in such a way as to minimize as far as possible the risk of the thrombogenic fibers coming loose from the embolization device.

The object is achieved by an embolization device with a main body and with at least one thrombogenic fiber, which main body can be converted from an elongate primary form to a secondary form, by the fact that the at least one thrombogenic fiber is arranged in a configuration wound around the main body. For a method for producing such an embolization device, the object is achieved by the fact that at least one thrombogenic fiber is wound around a primary coil forming a main body of the embolization device, and that the primary coil is converted to a secondary coil. Developments of the invention are defined in the dependent claims.

An embolization device is thus created in which, by virtue of thrombogenic fibers being wound around the main body, these fibers no longer protrude, or no longer protrude to any great extent, from the main body, such that undesired release is avoided here. By virtue of the at least one thrombogenic fiber being wound around the main body, the diameter of the main body is increased, such that the thrombogenic effect can be improved by reducing the spacing between the individual turns of a coil-shaped embolization device. A particularly good hold of the at least one thrombogenic fiber on the main body is achieved if the main body is not merely wire-shaped but also designed as a primary coil. In this way, even without at least one thrombogenic fiber being wound around it, the main body already has a greater diameter than would a main body formed merely from a wire. After thrombogenic fibers have been wound around it, the diameter is increased still further and the thrombogenic effect is therefore improved still further.

For the winding of fibers around the main body of the embolization device, it is particularly advantageous to provide an inner mandrel inside the main body. Such an inner mandrel makes it considerably easier to grip the main body, so as to be able to wind the thrombogenic fibers around it, than would be the case without such an inner mandrel, since the end of the latter can be gripped and the main body can be held straight in the longitudinal direction for the winding process.

In order to permit a particularly good hold for the at least one thrombogenic fiber on such a main body designed as a primary coil, the fiber is advantageously wound around the outside of the primary coil. In this connection, it proves particularly advantageous for a fiber bundle, or at least two fiber bundles, of thrombogenic fibers to be wound around the outside of the primary coil, since a better fiber join can be provided by provision of fiber bundles of this kind, and at the same time it is possible to reduce the risk of individual fibers protruding from the main body. Moreover, by using fiber bundles, the main body can be surrounded completely by thrombogenic fibers more quickly than would be possible with just a single thrombogenic fiber, and this proves advantageous in the production of the embolization device. The final diameter of the main body of the embolization device can be specifically defined by a suitable choice of the thickness of the fiber bundles and the number of layers wound around the main body.

The primary coil is advantageously formed from at least one wire-like element, and the at least one thrombogenic fiber is wound around the at least one wire-like element. In this embodiment variant, the at least one thrombogenic fiber is wound around the wire-like element not just after a main body in the form of a primary coil has been produced, but before the primary coil is wound up to form the main body. In this way, the primary coil is already formed with a greater diameter compared to a normal primary coil without such thrombogenic fibers. This main body can then be converted in the desired manner to the embolization device. Although further winding-on of additional thrombogenic fibers is possible, it is not absolutely essential. When at least one thrombogenic fiber is wound around the wire-like element used to produce the main body in the form of a primary coil, the risk of such a thrombogenic fiber coming loose is even less than in the previously described variant in which at least one thrombogenic fiber is wound only subsequently around the primary coil of the main body. The reason for this is that, when the thrombogenic fiber is wound around the wire-like element, said fiber is bound even more firmly into the primary coil as the latter is subsequently wound up, with the result that, after the subsequent conversion of the primary coil or of the main body of the embolization device to the secondary configuration, for example a helix, the at least one thrombogenic fiber cannot easily come loose from the embolization device.

It proves advantageous to secure the end of the at least one thrombogenic fiber on the main body. This also avoids the risk of the thrombogenic fiber accidentally coming loose again from the main body and possibly unwinding from the main body. It proves particularly advantageous in this respect if the at least one thrombogenic fiber is secured, in particular knotted, to an end loop of an inner mandrel of the primary coil. The primary coil surrounds the inner mandrel, which at the end is formed into a loop in order to allow the embolization device to be engaged by a positioning system.

Moreover, the at least one thrombogenic fiber can advantageously be wound around part of the inner mandrel of the primary coil, in particular an end loop of the inner mandrel. It is in this case also possible to secure the at least one thrombogenic fiber on the end loop of the inner mandrel, or on the inner mandrel, such that undesired detachment from the inner mandrel or main body of the embolization device can again be avoided in this way.

It proves particularly advantageous when an embolization device with a main body, which main body can be converted from an elongate primary form to a secondary form, is designed in such a way that the main body is designed as a primary coil with inner mandrel, in which case the inner mandrel has differently shaped loops at its ends. These differently shaped end loops can then be used for engagement by a positioning system, such that they can advantageously be adapted to the latter. In particular, the proximal loop can be designed to secure retention wires and similar devices in order to hold and direct these before and during the release from a catheter through which the embolization device is conveyed to the implantation site. The distal loop can be designed for engagement of other retention wires or guide devices, such that optimal engagement of the embolization device is also possible here.

In particular, the inner mandrel can be designed flexibly, especially as a flat element, in the area of one end loop (the distal loop). By contrast, in the area of the other end loop (the proximal loop), it is advantageous for the inner mandrel to be substantially stiff, and in particular provided with a round or oval material cross section, so as to permit connection to a positioning system. Other configurations are of course also possible in principle, and, as has already been mentioned, adaptation to retention devices and guide devices can be provided in order to direct the embolization device in the best possible way at the implantation site and then be able to release it. For this purpose, a substantially stiff design of the loop is suitable in order to permit easy guidance by a positioning system. The distal loop advantageously designed as a flat element is first pushed out of a catheter during placement of the embolization device and should therefore emerge at the implantation site as far as possible without causing injury. Therefore, a more flexible design is suitable here than at the other loop (proximal loop), which is made stiffer in order to permit guidance.

To place the embolization device in position, a positioning system can advantageously be used that comprises at least one positioning device with a retention wire extending through same, which retention wire is substantially stiff, in order to hold a proximal end of the embolization device and to stabilize and direct the embolization device during its advance through the inside of a catheter and out of the latter, and is designed to be detachable in order to release the embolization device from the proximal end of the embolization device. By means of such a positioning system, the embolization device can be advanced particularly easily through a catheter and released at an implantation site.

Particularly good stabilization to avoid kinking of the positioning device and/or of the primary coil of the embolization device can be achieved by provision of at least one connection piece with a portion that can be secured on the primary coil of the embolization device or can engage thereon with a force fit, a device connectable to the retention wire, and a portion that can fit into the positioning device or can engage on the latter with a force fit. The connection piece is advantageously made of a material that is compatible for the patient, in particular of nitinol or another biocompatible material. The connection piece can have a nose-like projection for engaging in a pusher coil of the positioning system. A particularly good and reliable connection to the pusher coil is made possible in this way.

The device connectable to the retention wire is advantageously an opening in the connection piece. The retention wire can be guided through this opening, and a connection to the primary coil can be established in this way. For this purpose, the retention wire advantageously comprises a loop portion and an elongate portion that can be threaded through the loop portion. The loop portion can thus be threaded through the opening in the connection piece, and the elongate portion can be threaded through the loop of the loop portion, with the result that, by pulling on the loop portion, a firm hold on the connection piece is possible by interaction with the elongate portion.

The portion that can be secured on the primary coil of the embolization device advantageously has an outer thread or outer ribs and/or grooves for engagement of windings or for engagement in interstices between windings of the primary coil. Such a portion can be easily screwed into the proximal end of the primary coil and secured firmly therein, such that a firm and stable connection to the pusher coil of the positioning system can be achieved.

In order to connect the primary coil of an embolization device and the positioning system, a connection piece is advantageously first of all screwed into the proximal end of the primary coil of the embolization device, a loop portion and an elongate portion of a retention wire are advanced by a pusher coil of the positioning system, the loop portion is pushed through an opening in the connection piece, the elongate portion is threaded through the loop portion, a tensile force exerted on the loop portion causes the latter to interact with the elongate portion and hold securely on the connection piece, and further application of a tensile force draws the pusher coil and primary coil toward each other and causes the nose-like projection of the connection piece to engage in the distal end of the pusher coil.

In order to release the primary coil of an embolization device from a positioning system, a connection piece engaging in the primary coil and in a pusher coil of the positioning system is provided which is held by the intermeshing loop portion and elongate portion of a retention wire extending through the pusher coil, and in which the loop portion protrudes through an opening in the connection piece and interacts with the elongate portion and is held securely thereon, and the elongate portion is withdrawn from the loop portion, the loop portion is pulled out of the opening in the connection piece, the pusher coil is withdrawn into a catheter, and in doing so the portion of the connection piece engaging in the pusher coil is pulled out of the latter.

When pushing the primary coil of the embolization device through a catheter by means of a pusher coil serving as positioning device, considerable forces occur that may lead to a kinking of the coils. For this reason, the provision of the connection piece, which engages in the primary coil and causes stiffening in the end area thereof and also leads to better transmission of forces there and at the pusher coil on which it also engages, proves to be particularly advantageous. The retention wire in the form of the loop portion and of the elongate portion serves, on the one hand, to secure the pusher coil or positioning device on the primary coil and, on the other hand, to keep the connection between the two coils straight and, of course, permit controlled detachment of the positioning device from the embolization device when the latter is to be released. Thus, the provision of such a connection piece between a primary coil and a positioning device, which connection piece engages on both of these and facilitates the transmission of force by stiffening the connection between both of them, proves to be extremely advantageous even independently of the embolization device according to the present invention.

To permit connection to the retention wire, however, the proximal end of the embolization device can also be provided with an end loop instead of the connection piece. This end loop can be part of an inner mandrel, as has already been described above, or can be provided there separately from the latter. Engagement of the loop portion and connection with the aid of the elongate portion of the retention wire is also possible in principle upon provision of such an end loop.

Another advantageous embodiment of an embolization device with a main body, which main body can be converted from an elongate primary form to a secondary form, is one in which the coil-shaped secondary form has a first conically narrowing coil portion, an approximately cylindrical portion adjoining the end of lesser diameter of the conically narrowing portion, and a third portion which starts from the cylindrical portion and extends on the outside of the first conically narrowing coil portion in the direction of the end of greater diameter thereof and is wound at least partially around same. In this way, in principle, a largely double-layered conically narrowing coil shape is obtained as the secondary form of the embolization device. The conically narrowing portion of the embolization device is formed from a plurality of superposed windings of the main body, such that this portion can be stabilized by this means. A greater density of the individual windings of the main body is also created here for the secondary form of the embolization device. The thrombogenic effect of the embolization device can be optimally increased in this way.

In all of the aforementioned embodiments, it proves advantageous if the main body is made of a metal and/or plastic. In particular, the main body can be made of a shape-memory material, in particular nitinol, or another shape-memory material. For the at least one thrombogenic fiber, it is suitable in particular to use synthetic fibers or filaments. The synthetic fibers can be chosen particularly advantageously from the group comprising absorbent and non-absorbent materials, natural and synthetic fabrics, in particular polyester, polyamide, polypropylene, polybutyl ester, expanded polytetrafluoroethylene (ePTFE), polyvinylidene fluoride (PVDF), nylon, cloth, silk, catgut.

The inner mandrel can advantageously have a screw-shaped profile or a profile provided with outer protuberances. In this way, it fits optimally into the primary coil of the main body, such that the individual windings of the primary coil can engage on the screw-shaped inner mandrel or on the inner mandrel provided with outer protuberances.

It also proves very advantageous if the primary coil is wound from at least one wire-like element, and the windings are arranged closely adjacent to one another. When winding at least one thrombogenic fiber or a thrombogenic fiber bundle around the primary coil as main body of the embolization device, a particularly good hold can be obtained if the windings of the primary coil are arranged closely adjacent to one another. The winding process itself is also easier to carry out than in the case where the primary coil has turns set at a greater distance from one another. It is of course possible, in principle, to use primary coils whose windings are not arranged so closely adjacent to one another, but in most cases a primary coil with windings arranged closely adjacent to one another will be preferred over this.

Figure 2:
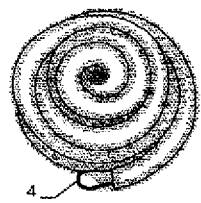
Figure 3:
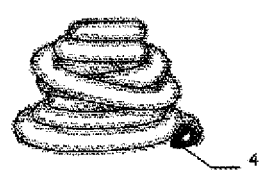
Figure 4:
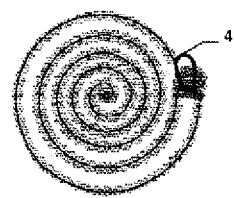
Figure 5:
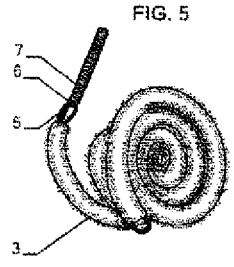
Figure 6:
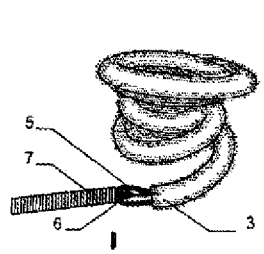
Figure 7:
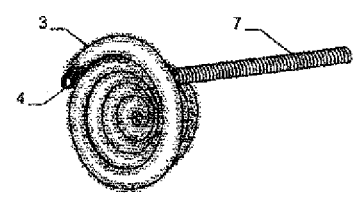
Figure 15:
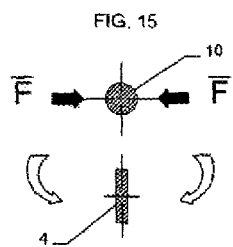
Figure 16:
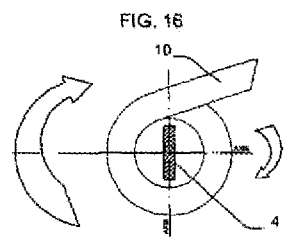
Figure 17:
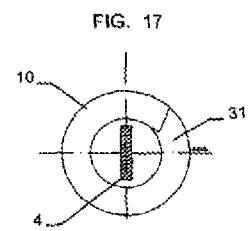
Figure 18:
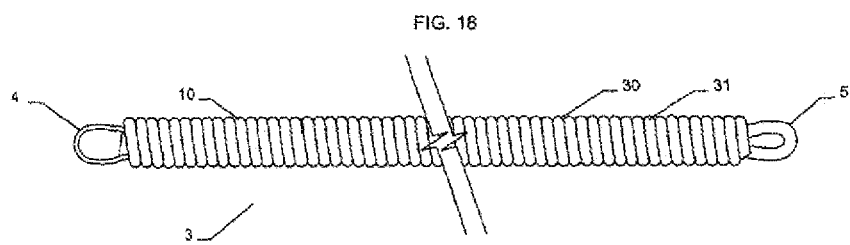
Figure 19:
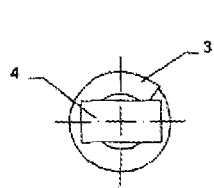
Figure 20:
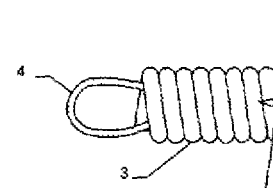
Figure 21:
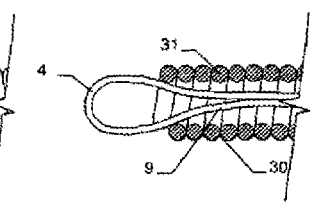
Figure 22:
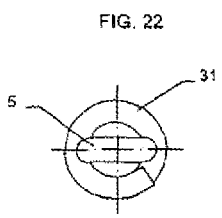
Figure 23:
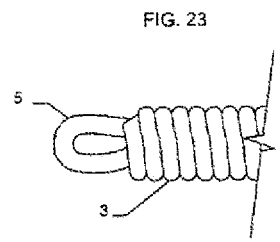
Figure 24:
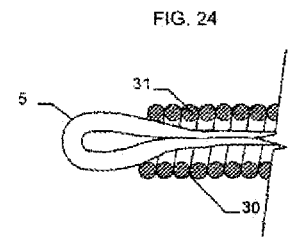
Figure 25:
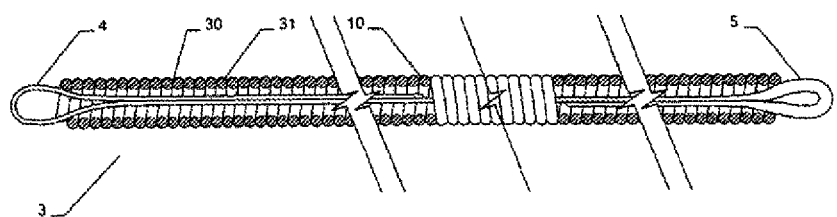
Figure 26:
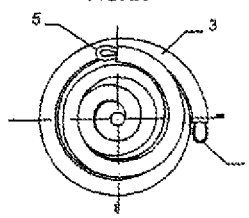
Figure 27:
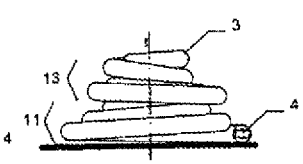
Figure 28:
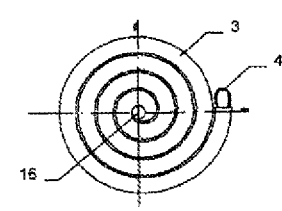
Figure 29:
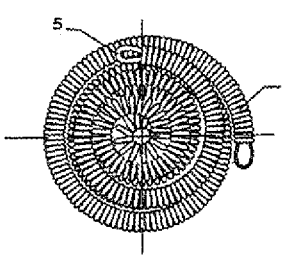
Figure 30:
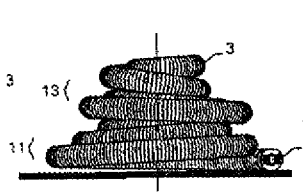
Figure 31:
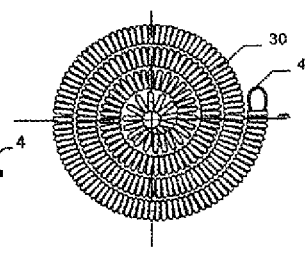
Figure 32:
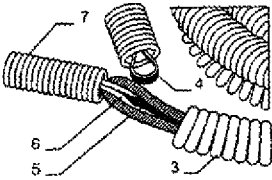
Figure 33:
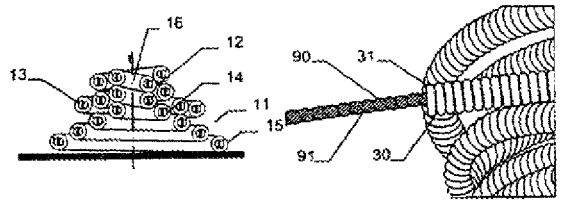
Figure 34:
Figure 54:
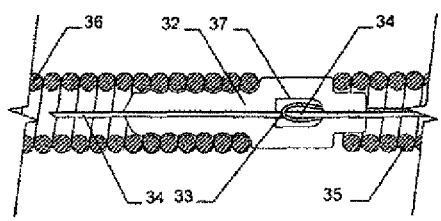
Figure 55:
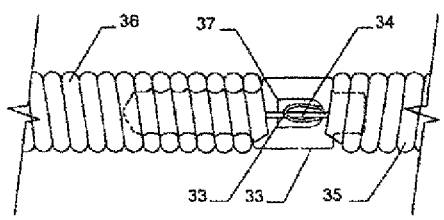
Figure 56:
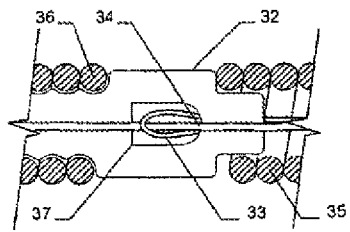
Figure 57:
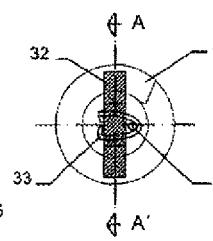
Figure 58:
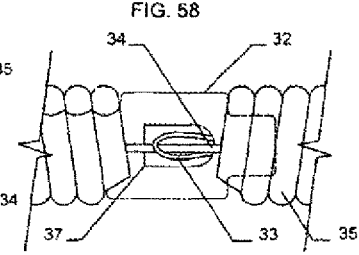
Figure 59:
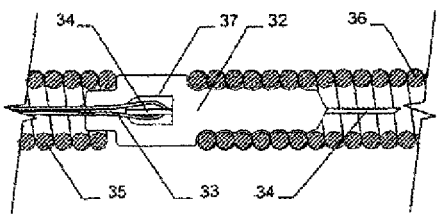
Figure 60:
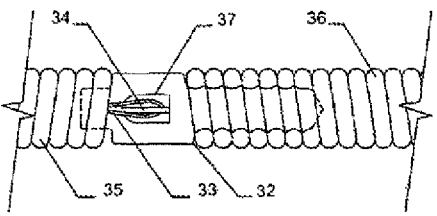
Figure 61:
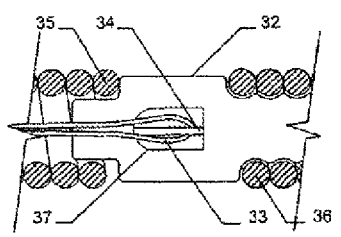
Figure 62:
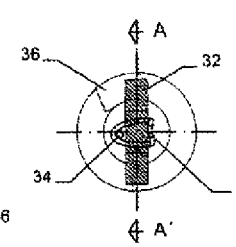
Figure 63:
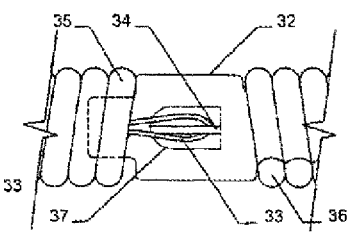

The invention is explained in greater detail below on the basis of illustrative embodiments and by reference to the drawings, in which:

FIG. 1 shows a perspective view of a first embodiment of an embolization device according to the invention, in the form of a conically narrowing embolization coil, FIG. 2 shows a plan view of the embolization coil according to FIG. 1, FIG. 3 shows a side view of the embolization coil according to FIG. 1, FIG. 4 shows a bottom view of the embolization coil according to FIG. 1, FIG. 5 shows a perspective view of the embolization coil according to FIG. 1, obliquely from below and with a positioning device secured to the end thereof, FIG. 6 shows a perspective side view of the embolization coil according to FIG. 5, FIG. 7 shows a perspective bottom view of the embolization coil according to FIG. 5, FIG. 8 shows a detail of a main body of an embolization device according to the invention during the process of securing thrombogenic fibers to the main body, FIG. 9 shows a side detail of the main body according to FIG. 8 partially arranged in a catheter and with a thrombogenic fiber partially wound thereon, FIG. 10 shows an enlarged detail of a main body according to FIG. 8 designed as a primary coil, with two thrombogenic fiber bundles wound partially around the outside thereof, FIG. 11 shows a detail of a main body designed as a primary coil for an embolization device according to the invention, with an end loop which is gripped by a retention wire of a positioning system, and with a fiber bundle wound partially around the outside thereof, FIG. 12 shows a detail of the main body and of the positioning system according to FIG. 11, with an end of the fiber bundle being secured on the main body in the area of the loop, FIG. 13 shows a detail of the main body with an end loop in which the positioning system engages, with the thrombogenic fibers being secured on the loop by being wound around it, FIG. 14 shows a perspective view of the embolization coil according to FIG. 1, secured on a retention wire of a positioning system, FIG. 15-FIG. 17 are diagrams showing the process of winding a primary coil for a main body of an embolization device according to the invention, having an inner mandrel with end loops, FIG. 18 shows a plan view of a finished main body of an embolization device according to the invention, the main body having an inner mandrel with end loops, FIG. 19 shows a plan view of one end loop of the inner mandrel, which loop is substantially flat, FIG. 20 shows a detail of the end of the portion of the main body with the loop shown as a flat element in the plan view in FIG. 19, FIG. 21 shows a cross-sectional view of the detail according to FIG. 20, FIG. 22 shows a plan view of the other end loop of the inner mandrel according to FIG. 18, which loop has an approximately round material cross section, FIG. 23 shows a detail of the portion of the main body with the loop shown in the plan view in FIG. 22, FIG. 24 shows a cross-sectional view of the detail according to FIG. 23, FIG. 25 shows a partially sectioned plan view of the main body with inner mandrel and end loops according to FIG. 18, FIG. 26 shows a plan view of an embolization coil, formed from the main body according to FIGS. 18 and 25, in a secondary form, FIG. 27 shows a side view of the embolization coil according to FIG. 26, FIG. 28 shows a bottom view of the embolization coil according to FIG. 26, FIG. 29 shows a plan view of the embolization coil according to FIG. 26, with a detailed depiction of the main body forming the primary coil, FIG. 30 shows a side view, corresponding to FIG. 27, of the embolization coil according to FIG. 26, with a detailed depiction of the main body forming the primary coil, FIG. 31 shows a bottom view, corresponding to FIG. 28, of the embolization coil according to FIG. 26, with a detailed depiction of the main body forming the primary coil, FIG. 32 shows a detail of the engagement of a retention wire in one end loop of the inner mandrel of the embolization coil, FIG. 33 shows a cross-sectional side view of the embolization coil according to FIG. 26 in the depiction according to FIG. 27, FIG. 34 shows a detail of the embolization coil according to FIGS. 26 and 29, with the screw-shaped inner mandrel pulled out, FIG. 35 shows a detail of a pusher coil of the positioning device in elongate form, FIG. 36 shows a detail of a retention wire of the positioning system, FIG. 37 shows a detail of a connection piece for engaging in one end of an embolization coil, FIG. 38 shows a detail of a second embodiment of a connection piece for engaging in an embolization coil, FIG. 39 shows an enlarged detail of the connection piece according to FIG. 38, FIG. 40 shows a plan view of an embolization coil, with a connection piece before engagement in one end of the embolization coil, FIG. 41 shows a detail of the loop portion of the retention wire according to FIG. 36, FIGS. 42 to 47 show details of the process by which the embolization coil with connection piece according to FIG. 40 is gripped by the retention wire arranged inside the pusher coil, FIGS. 48 to 53 show details of a process by which the embolization coil according to FIG. 40 with inserted connection piece is detached from a pusher coil with a retention wire arranged therein, FIG. 54 shows a sectional view through a detail of an embolization coil and pusher coil connected to each other by a connection piece and retention wire, FIG. 55 shows a side view of the detail according to FIG. 54, FIG. 56 shows a sectional view of the detail of the connection between connection piece and retention wire, FIG. 57 shows a transverse sectional view of the detail according to FIG. 56, FIG. 58 shows a side view of the detail according to FIG. 56, FIG. 59 shows a cross-sectional view of the detail according to FIG. 54 from the rear, FIG. 60 shows a side view of the detail according to FIG. 59, FIG. 61 shows a cross-sectional view of the detail according to FIG. 56 from the rear, FIG. 62 shows a cross-sectional view of the detail according to FIG. 61, and FIG. 63 shows a side view of the detail according to FIG. 61.

FIG. 1 shows a perspective view of a first embodiment of an embolization coil 1 with thrombogenic fibers 2. The thrombogenic fibers 2 are wound around the outside of a main body 3 of the embolization coil 1. At the ends, the main body 3 has loops 4, 5 which protrude from the wound portion and which, as will be explained below, are part of an inner mandrel. At least the loop 5 serves to secure a positioning system, as is indicated in FIGS. 5 to 7. A retention wire 6 of a positioning device 7 can engage in the loop 5 in order, on the one hand, to hold the embolization coil and, on the other hand, to be able to direct it during the release process.

It is also possible, however, to engage the embolization coil at the other loop 4, the latter being arranged at an end of the embolization coil, whereas the loop 5 is arranged on the outside of the embolization coil, in the area of the conically narrowing portion thereof.

As can be seen in particular from the plan view, the side view and the bottom view of the embolization coil according to FIGS. 2 to 4, the winding of thrombogenic fibers around the main body results in a particularly tight implant, which is therefore particularly suitable for producing a thrombus at the desired location in the body of a human or animal. As will also be seen from these figures, and in contrast to the prior art, no thrombogenic fibers protrude from the main body of the embolization coil, or from the latter, such that there is no longer any risk, or at least hardly any risk, of thrombogenic fibers that protrude in this way in the prior art migrating through the blood stream of a human or animal.

In addition to the provision of thrombogenic fibers, the particular configuration of the conically narrowing embolization coil, which has a double layer in a middle area, also results in a particularly tight body, which further assists the embolization process. This particular configuration is discussed in more detail below with reference to FIGS. 26 to 33.

FIGS. 8 to 13 show the process by which the main body 3 of the embolization coil is wound up as a primary coil. FIG. 8 shows the initial knotting of bundles of thrombogenic fibers on the main body 3. After they have been secured at the end on the main body, as is shown in FIG. 8, the fiber bundles are wound around the outside thereof, as is shown in FIG. 10. The two fiber bundles shown in FIG. 10 can be wound parallel to each other and in the same direction around the outside of the main body 3 forming the primary coil. In principle, it is possible for different fiber bundles to be wound in opposite directions around the main body. In the view in FIG. 9, thrombogenic fibers or fiber bundles have already been wound around part of the main body. The winding can be carried out in several layers or in just one layer, with either just one fiber bundle or several fiber bundles, or even with just one thrombogenic fiber, depending on the chosen material thickness of the thrombogenic fiber or thrombogenic fibers or of the fiber bundles and of the primary coil of the main body. For example, a different winding diameter of the thrombogenic fibers can also be provided along the longitudinal extent of the main body, in other words a winding can be made partially with several layers or with fibers of greater diameter.

In the view according to FIG. 11, it will be seen that a wide bundle of fibers has been wound around the main body 3 almost as far as the end of the primary coil thereof. The loop 5 of the inner mandrel protrudes from the main body. This loop 5 is gripped by the retention wire 6 arranged inside the positioning device 7, which is likewise coil-shaped. The positioning device is arranged inside a catheter 8, which is also indicated in FIG. 11 and FIG. 12. It can be seen quite clearly from FIG. 11 that, by winding the thrombogenic fibers 2 around the main body 3, a marked increase in cross section can be obtained which, when the main body has been converted to the secondary form of the embolization coil, results in the good thrombogenic action of said embolization coil.

To be able to secure the thrombogenic fibers or fiber bundles 2 on the main body 3, they are knotted at the ends on the main body, as is shown in FIG. 12. Although another form of securing is of course also possible here, the provision of fibers or fiber bundles makes knotting preferable because of the ease of this securing method.

In contrast to knotting or otherwise securing the fibers or fiber bundles 2 on the main body 3, FIG. 13 shows a variant in which the fibers 2 are secured on the loop 5 of the inner mandrel. The securing is achieved here by winding them around part of the loop 5. After they have been wound around the loop 5, the fibers 2 are also knotted, welded or secured in some other way. For example, the fiber bundle can be wound back a distance along the main body in order to surround the main body around which thrombogenic fibers have already been wound, and it can then be secured thereon in a suitable way. The method of securing the thrombogenic fibers or fiber bundles on the main body or on the inner mandrel thereof is advantageously chosen specific to the particular use, care being taken to ensure that no protruding ends of the thrombogenic fibers remain, as these could have negative effects on the embolization behavior of the embolization coil.

FIG. 14 shows the embolization coil according to FIG. 1 arranged on the positioning device 7 and held by the retention wire 6, said positioning device 7 being arranged together with the retention wire 6 inside the catheter 8. As can also be seen from FIG. 14, the embolization coil 1 forms a very compact unit, which has a particularly good embolization action.

FIGS. 15 to 17 show the process by which fibers are wound around the inner mandrel 9 provided with end loops 4, 5. Here, a wire-like element 10 is wound around the inner mandrel 9, specifically in the manner shown in FIGS. 15 and 16. This results in a number of windings 31 that are arranged closely adjoining one another and together form the primary coil 30 of the main body 3. This can be seen from the plan view of the main body 3 according to FIG. 18. As can be seen in particular from the partial cross section according to FIG. 25, which otherwise corresponds to the view in FIG. 18, the inner mandrel 9 extends in two layers in the end area, and over a relatively large portion of the main body, in order to form the loops 4, 5. In this way, this portion of the main body is additionally strengthened. The length of this double-layer portion of the inner mandrel 9 can thus be used to adjust the stiffness of the main body. If the latter is intended to be stiffer only in the outermost end area, the inner mandrel is doubled only in said area, whereas, if the main body is to be stiffer over a greater portion, the inner mandrel can be doubled along a greater portion.

As can be seen from the details in FIGS. 19 to 24, the two loops 4, 5 have different configurations. The loop 4 is flatter and wider than the loop 5, which has a substantially round material cross section. As can be seen in particular from the sectional end views in FIGS. 21 and 24, the inner mandrel is flat and slightly wider in the area where the loop 4 is formed or is to be formed, whereas the inner mandrel, in order to form the loop 5, is thicker in this area and has a thinner cross section inside the primary coil 30, that is to say the material of the inner mandrel is thicker in order to form the loop 5 and thus has a greater material cross section. This makes it very easy to engage the loop 5, since the latter has sufficient stability to be engaged. At the same time, there is no risk here of the retention wire being kinked by the flat, wide shape of the loop 4 and thus becoming caught when pulled back into the catheter for releasing the embolization coil.

FIGS. 26 to 28 and FIGS. 29 to 31 each show the principle by which the main body 3 is wound up into the secondary form of the embolization coil 1. As can be seen from the plan view according to FIGS. 26 and 29, but in particular from the side view according to FIGS. 27 and 30 and the sectional side view according to FIG. 33, the coil-shaped secondary form of the embolization coil is formed initially by winding of a first conically narrowing coil portion 11, which is adjoined by a second, approximately cylindrical portion 12. The connection is made at the end 14 of the conically narrowing coil portion, which has a smaller diameter than the end 16. The second, cylindrical portion 12 has a slightly smaller diameter than the end 14 of the conically narrowing coil portion 11. This can be seen particularly well in FIG. 33. The cylindrical portion 12 is adjoined by a third portion 13, which is formed by being wound in the direction of the end 15 of greater diameter of the conically narrowing coil portion 11, on the outside thereof, thus surrounding the cylindrical portion and, if appropriate, also part of the conically narrowing coil portion. As can be seen from FIG. 33, the individual windings of the third portion 13 can also overlap one another and thus make available a particular tight packing of windings of the embolization coil. This not only achieves a particularly good thrombogenic action, but also a particularly high degree of stability in this narrower portion of the embolization coil. At the same time, the third portion 13 can provide a particularly good hold in the respective body opening that is to be closed by the embolization coil, since a suitable shaping of the third portion, that is to say a suitable arrangement of the windings, allows certain areas of the embolization coil to be made particularly stable, and at least some of the windings can extend farther out than others. As can be seen from FIGS. 27, 30 and 33, it is here the last winding of the portion 13 that carries the loop 5.

As can be seen from the views of the embolization coil 1 according to FIGS. 28 and 31, which each show a bottom view of this embolization coil, the latter is shaped regularly as a coil when seen from the underside, that is to say looking at the conically narrowing coil portion from below, and is provided with or lacks a central opening 16, indicated in FIG. 33 and FIG. 28. In particular, once thrombogenic fibers or fiber bundles have been wound around the primary coil 30, as is shown in FIGS. 1 to 14, this inner opening 16 is thus closed, such that the embolization effect can be optimized. This can also be seen in particular from FIGS. 2 and 4. By comparing FIGS. 2 and 29, FIGS. 3 and 30 and FIGS. 4 and 31, it will be immediately evident that, by winding thrombogenic fibers 2 around the embolization coil or the primary coil 30 thereof, a more compact and tighter unit can be created which has a very much greater embolization effect than the embolization coil without such thrombogenic fibers.

FIG. 32 shows a corresponding connection between the retention wire 6 of the positioning device 7 and the loop 5 of the inner mandrel 9 of the main body 3 of the embolization coil, as is already shown in FIG. 13, but here without thrombogenic fibers wound around it. The connection of the main body to the retention wire or positioning device 7 is therefore achieved in the same way as in the variant in which thrombogenic fibers surround the main body. As will be clearly evident from a comparison of FIGS. 13 and 32, however, by winding fibers around the ends of the main body of the embolization coil, a more compact and tighter unit is also achieved here, which at the same time has a greater diameter and can be used better for the embolization effect than the variant without such thrombogenic fibers.

FIG. 34 shows the inner mandrel 9 which is extended out from the primary coil 30 and which is screw-shaped in this embodiment variant, such that the individual windings of the primary coil 30 can better support themselves thereon. Instead of a screw-shaped inner mandrel, it is also possible, for example, to use an inner mandrel with protuberances on its outer face, in which case the windings of the primary coil 30 can then engage in respective grooves between the protuberances.

FIG. 35 shows a side view of a detail of a pusher coil 35 of the positioning device, into which a retention wire with a loop portion 33 and an elongate portion 34 (FIG. 36) can be inserted. FIG. 41 shows, on an enlarged scale, the detail of the loop portion 33 of the retention wire. For connection to an embolization coil, two embodiments of a connection piece 32 are shown in FIGS. 37 to 39. Both embodiments are flat and have a head part 39, with a central opening 37 and a nose like projection 38, and a portion 40 with outer ribs. The embodiment shown in FIG. 37 ends with a portion 40, whereas the embodiment according to FIGS. 38 and 39 has, adjoining the portion 40, a long straight portion 42, without outer ribs, and a dot-shaped end portion 41. The long straight portion 42 can extend through a primary coil of an embolization coil, in which case the end portion 41 then protrudes instead of the loop 5 from the primary coil. The connection piece 32 can be made of nitinol or another suitable material and can be produced from a sheet of metal by laser cutting.

FIG. 40 shows a plan view of an embolization coil 1 in wound-up form, in which one end of the primary coil 36 is left open to allow the connection piece 32 to be inserted therein. The process of inserting the connection piece and of joining it to the pusher coil 35 is shown in FIG. 42 et seq. and is described below with reference thereto.

FIG. 42 shows a proximal end of the primary coil 36 of the embolization coil, the connection piece 32, with the portion 40 with outer ribs facing in the direction of the primary coil 36, and a distal end of the pusher coil 35 with inserted retention wire, of which the loop portion 33 and the elongate portion 34 are shown. In the next step for joining the pusher coil and embolization coil (FIG. 43), so as to be able to better advance the latter through a catheter to the implantation site, the connection piece is screwed with the portion 40 into the primary coil 36, which is easy to do because of the outer ribs of the portion 40. The external diameter of said portion 40 is advantageously adapted to the internal diameter of the primary coil in this end area. The head part 39 lies outside the primary coil 36, the nose-like projection 38 is oriented in the direction of the pusher coil 35, from which the loop portion 33 and the elongate portion 34 are partly pushed out.

In a subsequent step, which is shown in FIG. 44, the loop portion 33 is pushed through the central opening 37 in the head part 39. In a further step, which is shown in FIG. 45, the long straight portion 42 is pushed through the loop portion 33. Thereafter, the elongate portion 34 is pulled (FIG. 46) until the nose-like projection 38 lies in the distal end of the pusher coil 35, as is shown in FIG. 47. A compact unit of primary coil and pusher coil can be created by means of the connection piece 32, since the nose-like projection 38 bears both on the pusher coil and also on the primary coil and engages therein. In this way, the transmission of force from the pusher coil to the primary coil during the advance of the primary coil through a catheter is achieved very much more easily than without the provision of such a connection piece 32. Without the latter, the coil(s) may buckle, which means that a controlled advance is no longer possible.

In addition to advancing the primary coil of the embolization coil through the catheter to the implantation site, the release of the embolization coil at the implantation site is also made easy by this means. As is shown in FIGS. 48 to 53, the release takes place in principle in the reverse order to the steps by which pusher coil and primary coil are joined via the connection piece 32.

A similar situation to that in FIG. 47 is shown in FIG. 48, in which the pusher coil 35, connection piece 32 and primary coil 36 are connected to one another with the aid of the retention wire. Here, the nose-like projection 38 still lies in the distal end of the pusher coil, and the loop portion 33 of the retention wire is pushed through the opening 37 of the connection piece 32 and held therein by the elongate portion 34 extending through it. In the next step of the release process, which is shown in FIG. 49, the elongate portion 34 has been withdrawn from the loop portion 33. In the further step shown in FIG. 50, the loop portion 33 is pulled out of the central opening 37 and the elongate portion 34 is withdrawn into the pusher coil 35. Thereafter, the pusher coil can be withdrawn into the catheter (not shown in FIG. 51), with the nose-like projection being pulled out of the distal end of the pusher coil. Pusher coil and primary coil are thus separated again. The primary coil can deform into its secondary form at the implantation site, such that the embolization coil assumes its desired shape. The pusher coil can be withdrawn farther into the catheter, as is shown in FIGS. 52 and 53.

In this way, the embolization coil can easily be released at the implantation site, and it is likewise possible in principle to obtain reconnection to that end of the embolization coil provided with the connection piece, e.g. for changing the position of the embolization coil at the implantation site or, if appropriate, also removing the embolization coil from there. For this purpose, the pusher coil 35 is advanced, in particular through a catheter, as far as the connection piece 32, the loop portion 33 is threaded into the central opening 37 in the connection piece 32, the elongate portion 34 of the retention wire is threaded through the loop of the loop portion, and then, by pulling on the loop portion 33, the primary coil is drawn toward the pusher coil. From the outside of the two coils 35, 36, it is possible to see only some of the head part 39 of the connection piece 32, with the loop portion 33 lying in the central opening 37 and with the elongate portion 34 threaded through the loop portion 33, as is shown in the side view in FIG. 55. FIG. 54 shows a corresponding sectional view in which it will be noted that the elongate portion 34 protrudes past the distal end of the connection piece into the primary coil, thus eliminating the danger of its slipping out of the loop portion during withdrawal into the pusher coil for securing on the connection piece 32.

FIGS. 56 to 58 show in greater detail the elongate portion 34 threaded through the loop portion 33. FIGS. 59 to 63 show the same connection from the rear, from which it will be clearly seen that the loop portion 33 is formed from a wire-like element formed into the loop. To form the loop portion 33 and elongate portion 34, it is possible to use just one retention wire which, for example, is turned back on itself twice with a loop, such that a free end (elongate portion 34) is obtained and a loop portion 33 likewise at this end.

This way of positioning and releasing an embolization device is suitable not only in an implant provided with plastic filaments, but also in other implants which can be pushed by a positioning device through a catheter and on which it is possible to mount a connection piece that engages both on the implant and also on the positioning device and permits stabilization of the connection between implant and positioning device and better transmission of force.

In addition to the embodiments of embolization coils described above and shown in the figures, many others are also possible in which thrombogenic fibers are wound, or at least one thrombogenic fiber wound, around the outside of the main body of the embolization coil, it being possible for the main body to have the form of a wire-like element and/or of a primary coil and/or another shape.

LIST OF REFERENCE SIGNS 1 embolization coil
2 thrombogenic fiber
3 main body
4 loop
5 loop
6 retention wire
7 positioning device
8 catheter
9 inner mandrel
10 wire-like element
11 conically narrowing coil portion
12 cylindrical portion
13 third portion, wound round the cylindrical portion
14 end of 11
15 end of 11
16 inner opening
30 primary coil
31 winding
32 connection piece
33 loop portion of a retention wire
34 elongate portion of a retention wire
35 pusher coil
36 primary coil
37 central opening
38 nose-like projection
39 head part
40 portion with outer ribs
41 end portion
42 long straight portion
90 protuberance
91 groove

What is claimed is:

1. An embolization device comprising:
an elongated curvaceous main body and at least one thrombogenic fiber, wherein the main body forms an elongate primary coil including windings, wherein the primary coil is convertible to a secondary coil, and wherein the at least one thrombogenic fiber is wound around the elongated curvaceous main body;
wherein the main body contains at least one inner mandrel having a distal end portion having a distal end loop and a proximal end portion having a proximal end loop and a body portion having a shape of a screw or outer protuberances forming grooves, wherein the primary coil windings engage in the grooves;
wherein the at least one inner mandrel and main body are configured to remain attached during use of the embolization device, including the primary coil windings engaged in the grooves;
wherein the distal end portion and the distal end loop of the at least one inner mandrel are flexible relative to the proximal end portion and the proximal end loop of the at least one inner mandrel, respectively, and have a planar cross section, wherein the planar cross section of the distal end loop forms at least a planar outer surface of the distal end loop;
wherein the proximal end portion and the proximal end loop of the at least one inner mandrel are stiff relative to the distal end portion and the distal end loop of the at least one inner mandrel, respectively, and have a round or oval cross section thicker than the planar cross section to connect to a positioning system;

wherein the at least one thrombogenic fiber is secured at an end on the main body; and wherein the at least one thrombogenic fiber is knotted on one of the end loops of the at least one inner mandrel.

2. The embolization device of claim 1, wherein the at least one thrombogenic fiber is wound around an outside of the primary coil.

3. The embolization device of claim 1 wherein the at least one thrombogenic fiber comprises at least one fiber bundle of thrombogenic fibers wound around an outside of the primary coil.

4. The embolization device of claim 1, wherein the primary coil is formed from at least one wire-like element, and the at least one thrombogenic fiber is wound around the at least one wire-like element.

5. The embolization device of claim 1, wherein the at least one thrombogenic fiber is wound around the distal end loop of the at least one inner mandrel.

6. The embolization device of claim 1 wherein the secondary coil has a first conically narrowing coil portion, a second, approximately cylindrical portion adjoining an end of lesser diameter of the conically narrowing coil portion, and a third portion which starts from the cylindrical portion and extends on an outside of the first conically narrowing coil portion in a direction of an end of greater diameter of the conically narrowing coil portion and is wound at least partially around the conically narrowing coil portion.

7. The embolization device of claim 1 wherein the main body is made of a metal and/or plastic.

8. The embolization device of claim 7 wherein the main body is made of a shape-memory material.

9. The embolization device of claim 1 wherein the at least one thrombogenic fiber is a natural or a synthetic fiber.

10. The embolization device of claim 1 wherein the at least one thrombogenic fiber is part of a fabric.

11. The embolization device of claim 1 wherein the at least one inner mandrel has a profile provided with outer protuberances and/or grooves.

12. The embolization device of claim 1, wherein the planar cross section of the distal end loop forms a planar inner surface of the distal end loop.

13. The embolization device of claim 1, wherein the planar outer surface of the distal end loop is perpendicular to a longitudinal axis of the inner mandrel.

14. The embolization device of claim 1, wherein the distal end loop is wider than the proximal end loop.

15. The embolization device of claim 1, wherein the distal end loop is thinner than the proximal end loop.

16. The embolization device of claim 1, wherein the distal end portion of the inner mandrel has only one distal end loop.

17. The embolization device of claim 1, wherein the proximal end portion of the inner mandrel has only one proximal end loop.

18. The embolization device of claim 1, wherein the at least one thrombogenic fiber is wound around an outside of the primary coil and does not protrude from between the windings of the primary coil.

19. A method for producing an embolization device comprising:

providing a main body and at least one thrombogenic fiber, wherein the main body is convertible from a primary coil including windings to a secondary coil, wherein the main body contains at least one inner mandrel having a distal end portion having a distal end loop and a proximal end portion having a proximal end loop, and a body portion having a shape of a screw or outer protuberances forming grooves, wherein the primary coil windings engage in the grooves;

wherein the mandrel and main body are configured to remain attached during use of the embolization device, including the primary coil windings engaged in the grooves;

wherein the distal end portion and the distal end loop of the at least one inner mandrel are flexible relative to the proximal end portion and proximal end loop of the at least one inner mandrel, respectively, and have a planar cross section, wherein the planar cross section of the distal end loop forms at least a planar outer surface of the distal end loop;

wherein the proximal end portion and proximal end loop of the at least one inner mandrel are stiff relative to the distal portion and the distal end loop of the at least one inner mandrel, respectively, and have a round or oval cross section thicker than the planar cross section to connect to a positioning system;

winding the at least one thrombogenic fiber around the primary coil of the main body;

knotting the at least one thrombogenic fiber on the distal end loop of the at least one inner mandrel; and converting the primary coil to the secondary coil.

20. The method of claim 19, wherein the at least one thrombogenic fiber comprises at least one fiber bundle of thrombogenic fibers wound around an outside of the primary coil.

21. The method of claim 19 further comprising securing the at least one thrombogenic fiber at an end of the main body.

22. The method of claim 19 wherein converting the primary coil to the secondary coil further comprising winding the primary coil to form the secondary coil, wherein the secondary coil has a first conically narrowing coil portion, a second, approximately cylindrical portion that adjoins an end of lesser diameter of the conically narrowing coil portion, and a third portion which extends in a direction of an end of greater diameter of the conically narrowing coil portion and is wound at least partially around an outside of the conically narrowing coil portion.

23. The method of claim 19 wherein the primary coil comprises a plurality of windings wound from at least one wire-like element, and the plurality of windings are arranged closely adjacent to one another.

* * * * *